(12) United States Patent
Sheldon et al.

(10) Patent No.: US 12,251,566 B2
(45) Date of Patent: Mar. 18, 2025

(54) RATE SMOOTHING TO ENHANCE ATRIAL SYNCHRONOUS PACING IN A VENTRICULAR PACEMAKER

(71) Applicant: Medtronic, Inc., Minneapolis, MN (US)

(72) Inventors: Todd J. Sheldon, North Oaks, MN (US); Wade M. Demmer, Coon Rapids, MN (US); Vincent P. Ganion, Blaine, MN (US); Juliana E. Pronovici, New Hope, MN (US); Vincent E. Splett, Apple Valley, MN (US); Menglong Xing, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/188,442

(22) Filed: Mar. 22, 2023

(65) Prior Publication Data
US 2023/0226360 A1    Jul. 20, 2023

Related U.S. Application Data

(63) Continuation of application No. 16/387,894, filed on Apr. 18, 2019, now Pat. No. 11,617,889.

(Continued)

(51) Int. Cl.
*A61N 1/365* (2006.01)
*A61N 1/362* (2006.01)
(Continued)

(52) U.S. Cl.
CPC ....... *A61N 1/3622* (2013.01); *A61N 1/36578* (2013.01); *A61N 1/36585* (2013.01);
(Continued)

(58) Field of Classification Search
CPC .. A61N 1/37512; A61N 1/368; A61N 1/3684; A61N 1/39622; A61N 1/36585;
(Continued)

(56) References Cited

U.S. PATENT DOCUMENTS 4,485,813 A    12/1984 Anderson et al.
5,052,388 A    10/1991 Sivula et al.
(Continued)

FOREIGN PATENT DOCUMENTS

CN    106102826 A    11/2016
CN    107073267 A    8/2017
(Continued)

OTHER PUBLICATIONS

Cooper, et al., "Absent Ventricular Tachycardia Detection in a Biventricular Implantable Cardioverter-Defibrillator due to Intradevice Interaction with a Rate Smoothing Pacing Algorithm", Heart Rhythm Society, vol. 1, No. 6, Dec. 1, 2004, 4 pages.
(Continued)

*Primary Examiner* — Deborah L Malamud

(57) ABSTRACT

A ventricular pacemaker is configured to determine a ventricular rate interval by determining at least one ventricular event interval between two consecutive ventricular events and determine a rate smoothing ventricular pacing interval based on the ventricular rate interval. The pacemaker is further configured to detect an atrial event from a sensor signal and deliver a ventricular pacing pulse in response to detecting the atrial event from the sensor signal. The pacemaker may start the rate smoothing ventricular pacing interval to schedule a next pacing pulse to be delivered upon expiration of the rate smoothing ventricular pacing interval.

20 Claims, 11 Drawing Sheets

Related U.S. Application Data

(60) Provisional application No. 62/660,704, filed on Apr. 20, 2018.

(51) Int. Cl.
*A61N 1/368* (2006.01)
*A61B 5/00* (2006.01)
*A61B 5/287* (2021.01)
*A61B 5/352* (2021.01)
*A61N 1/37* (2006.01)

(52) U.S. Cl.
CPC ....... *A61N 1/36592* (2013.01); *A61N 1/3682* (2013.01); *A61B 5/0031* (2013.01); *A61B 5/287* (2021.01); *A61B 5/352* (2021.01); *A61N 1/3706* (2013.01)

(58) Field of Classification Search
CPC .... A61N 1/3688; A61N 1/3702; A61N 1/362; A61N 1/3706; A61B 5/349; A61B 5/4836; A61B 5/352; A61B 5/7264; A61B 5/7282; A61B 5/0006; A61B 5/02; A61B 5/308; A61B 5/486; A61B 5/24; A61B 5/28; A61B 5/318
See application file for complete search history.

(56) References Cited

U.S. PATENT DOCUMENTS

| | | | |
|---|---|---|---|
| 5,507,782 A | 4/1996 | Kieval et al. | |
| 5,593,431 A | 1/1997 | Sheldon | |
| 5,792,193 A | 8/1998 | Stoop | |
| 5,885,471 A | 3/1999 | Ruben et al. | |
| 6,044,297 A | 3/2000 | Sheldon et al. | |
| 6,434,424 B1 | 8/2002 | Igel et al. | |
| 6,904,315 B2 | 6/2005 | Panken et al. | |
| 7,532,929 B2 | 5/2009 | Mussig et al. | |
| 7,801,607 B1 * | 9/2010 | Bornzin | A61N 1/3627 607/9 |
| 8,433,409 B2 | 4/2013 | Johnson et al. | |
| 8,532,785 B1 | 9/2013 | Crutchfield et al. | |
| 8,541,131 B2 | 9/2013 | Lund et al. | |
| 9,675,798 B2 | 6/2017 | Grubac et al. | |
| 10,207,116 B2 | 2/2019 | Sheldon et al. | |
| 2006/0265016 A1 | 11/2006 | Kim et al. | |
| 2007/0293899 A1 | 12/2007 | Sheldon et al. | |
| 2015/0196760 A1 | 7/2015 | Rajan et al. | |
| 2016/0114169 A1 | 4/2016 | Sheldon et al. | |
| 2016/0129262 A1 | 5/2016 | Sheldon | |
| 2016/0129263 A1 | 5/2016 | Demmer et al. | |
| 2016/0144190 A1 | 5/2016 | Cao et al. | |
| 2017/0368347 A1 | 12/2017 | Muessig et al. | |
| 2017/0368360 A1 | 12/2017 | Hahn et al. | |
| 2018/0085588 A1 | 3/2018 | Splett et al. | |
| 2018/0085589 A1 | 3/2018 | Splett et al. | |
| 2018/0117337 A1 | 5/2018 | Demmer et al. | |
| 2018/0161580 A1 | 6/2018 | Demmer et al. | |

FOREIGN PATENT DOCUMENTS

| | | |
|---|---|---|
| WO | 2018102639 A1 | 6/2018 |
| WO | 2019010353 A1 | 1/2019 |

OTHER PUBLICATIONS (PCT/US2019/028234) PCT Notification of Transmittal of the International Search Report and the Written Opinion of the International Searching Authority, Mailed Jul. 10, 2019, 13 pages.
"Office Action Issued in Chinese Patent Application No. 201980027073.0", Mailed Date: Jan. 26, 2024, 21 Pages.

* cited by examiner

RATE SMOOTHING TO ENHANCE ATRIAL SYNCHRONOUS PACING IN A VENTRICULAR PACEMAKER

RELATED APPLICATIONS

This application is a Continuation of U.S. patent application Ser. No. 16/387,894, filed Apr. 18, 2019, which claims priority to provisional U.S. Patent Application 62/660,704, entitled "Rate Smoothing to Enhance Atrial Synchronous Pacing in a Ventricular Pacemaker," filed on Apr. 20, 2018.

TECHNICAL FIELD

This disclosure relates to a ventricular pacemaker and a method for controlling ventricular pacing pulse timing for promoting atrial synchronous ventricular pacing.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two transvenous, intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some heart rhythm conditions, some patients may benefit from atrial and ventricular (dual chamber) sensing for providing atrial-synchronized ventricular pacing in order to maintain a more normal heart rhythm.

SUMMARY

The techniques of this disclosure generally relate to controlling ventricular pacing pulses delivered by a ventricular pacemaker to enhance atrial synchrony of the ventricular pacing pulses. The ventricular pacemaker may be an intracardiac ventricular pacemaker configured to sense atrial systolic events from within a ventricular chamber and deliver ventricular pacing pulses synchronized to the sensed atrial systolic events. A ventricular pacemaker configured to perform the techniques disclosed herein sets a rate smoothing pacing interval based on an actual ventricular rate interval determined from time intervals determined between consecutive ventricular events. When a ventricular pacing pulse is delivered synchronously with an atrial systolic event, the pacemaker starts the rate smoothing pacing interval and delivers the next ventricular pacing pulse upon expiration of the rate smoothing pacing interval in the absence of a sensed atrial systolic event during the rate smoothing pacing interval.

In one example, the disclosure provides a pacemaker including a pulse generator configured to deliver ventricular pacing pulses via electrodes coupled to the pacemaker; a sensor configured to produce a signal comprising atrial event signals; and a control circuit coupled to the sensor and the pulse generator. The control circuit is configured to determine a ventricular rate interval by determining at least one ventricular event interval between two consecutive ventricular events and determine a rate smoothing ventricular pacing interval based on the ventricular rate interval. The control circuit is further configured to detect an atrial event from the sensor signal, control the pulse generator to deliver a ventricular pacing pulse in response to detecting the atrial event from the sensor signal, and start the rate smoothing ventricular pacing interval to schedule the next pacing pulse to be delivered by the pulse generator upon expiration of the rate smoothing ventricular pacing interval.

In another example, the disclosure provide a method including determining a ventricular rate interval by determining at least one ventricular event interval between two consecutive ventricular events, determining a rate smoothing ventricular pacing interval based on the ventricular rate interval, detecting an atrial event from a sensor signal, delivering a ventricular pacing pulse in response to detecting the atrial event from the sensor signal, and starting the rate smoothing ventricular pacing interval to schedule a next pacing pulse to be delivered upon expiration of the rate smoothing ventricular pacing interval.

In yet another example, the disclosure provides a non-transitory, computer-readable storage medium comprising a set of instructions which, when executed by a control circuit of a pacemaker, cause the pacemaker to determine a ventricular rate interval by determining at least one ventricular event interval between two consecutive ventricular events and determine a rate smoothing ventricular pacing interval based on the ventricular rate interval. The instructions further cause the pacemaker to detect an atrial event from a sensor signal, deliver a ventricular pacing pulse in response to detecting the atrial event from the sensor signal, and start the rate smoothing ventricular pacing interval to schedule a next pacing pulse for delivery upon expiration of the rate smoothing ventricular pacing interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for controlling ventricular pacing, generally referred to as "rate smoothing," to avoid an abrupt change in ventricular rate and promote atrial synchronous ventricular pacing. In the illustrative examples presented herein, an intracardiac ventricular pacemaker is configured to sense atrial systolic events for synchronizing the ventricular pacing pulses to the atrial rate. As described below, the atrial systolic events may be sensed from a signal produced by a motion sensor that includes an atrial systolic event signal corresponding to atrial mechanical contraction and the active filling phase of the ventricle, sometimes referred to as the "atrial kick." In other examples, atrial systolic event sensing may be performed using other techniques, such as sensing the atrial systolic event from another cardiac mechanical signal (e.g., a pressure signal, acoustical signal, impedance signal, etc.) or sensing the P-wave of a cardiac electrical signal that is attendant to atrial depolarization.

The techniques disclosed herein provide rate smoothing by controlling the timing of a ventricular pacing pulse in the absence of an atrial sensed event. By controlling the ventricular pacing pulse delivery according to a rate smoothing interval, the ventricular pacing pulse is less likely to interfere with sensing of the next atrial event, increasing the likelihood of an atrial synchronized ventricular pacing pulse on the next cardiac cycle. In this way, the rate smoothing techniques disclosed herein tend to increase the percentage of ventricular pacing pulses that are delivered synchronously with the atrial rate, providing the patient with the benefits of atrial synchronized ventricular pacing without requiring electrodes or other sensors placed in or on the atrial chambers.

Figure 1:
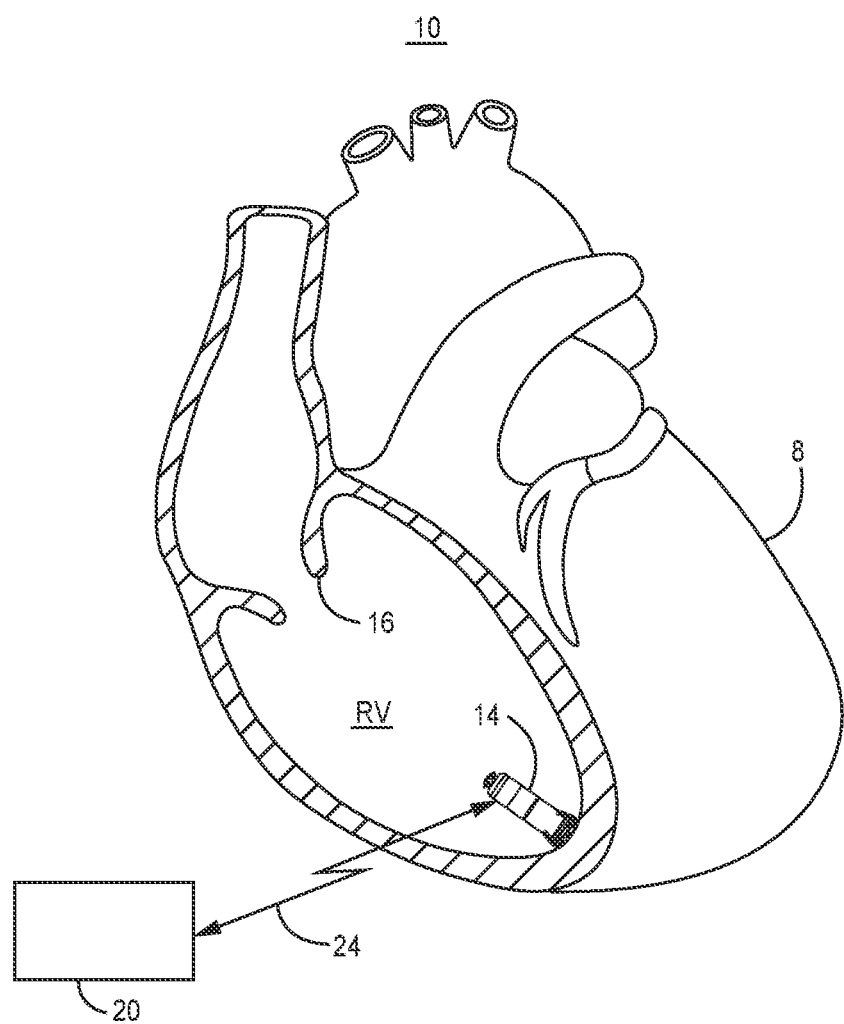
FIG. 1 is a conceptual diagram illustrating an intracardiac pacing system that may be used to sense cardiac electrical signals and motion signals induced by cardiac motion and flowing blood and provide pacing therapy to a patient's heart.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. IMD system 10 includes a right ventricular (RV) intracardiac pacemaker 14. Pacemaker 14 may be a transcatheter intracardiac pacemaker which is adapted for implantation wholly within a heart chamber, e.g., wholly within the RV or wholly within the left ventricle (LV) of heart 8 for sensing cardiac signals and delivering ventricular pacing pulses. Pacemaker 14 is reduced in size compared to subcutaneously implanted pacemakers and may be generally cylindrical in shape to enable transvenous implantation via a delivery catheter.

Pacemaker 14 is positioned along an endocardial wall of the RV, e.g., near the RV apex though other locations are possible. The techniques disclosed herein are not limited to the pacemaker location shown in the example of FIG. 1 and other positions within heart 8 are possible. For example, a ventricular intracardiac pacemaker 14 may be positioned in the LV and configured to detect cardiac motion signals and deliver atrial-synchronized ventricular pacing to the LV using the techniques disclosed herein. Pacemaker 14 may be positioned within the right ventricle or left ventricle to provide respective right ventricular or left ventricular pacing and for sensing motion signals by a motion sensor within the ventricular chamber.

Pacemaker 14 is capable of producing electrical stimulation pulses, e.g., pacing pulses, delivered to heart 8 via one or more electrodes on the outer housing of the pacemaker. Pacemaker 14 is configured to deliver RV pacing pulses and sense an RV cardiac electrical signal using housing based electrodes for producing an RV electrogram (EGM) signal. The cardiac electrical signals may be sensed using the housing based electrodes that are also used to deliver pacing pulses to the RV.

Pacemaker 14 is configured to control the delivery of ventricular pacing pulses to the RV in a manner that promotes synchrony between atrial activation and ventricular activation, e.g., by maintaining a target atrioventricular (AV) interval between atrial events and ventricular pacing pulses. That is, pacemaker 14 controls pacing pulse delivery to maintain a desired AV interval between atrial contractions corresponding to atrial systole and ventricular pacing pulses delivered to cause ventricular depolarization and ventricular systole.

According to the techniques described herein, atrial systolic events producing the active ventricular filling phase are detected by pacemaker 14 from a motion sensor such as an accelerometer enclosed by the housing of pacemaker 14. The motion signal produced by an accelerometer implanted within the RV includes motion signals caused by ventricular and atrial events. For example, acceleration of blood flowing into the RV through the tricuspid valve 16 between the RA and RV caused by atrial systole is detected by pacemaker 14 from the signal produced by an accelerometer included in pacemaker 14. Other motion signals detected by pacemaker 14, such as motion caused by ventricular contraction, motion caused by ventricular relaxation, and motion caused by passive filling of the ventricle are described below in conjunction with FIG. 4.

In other examples, pacemaker 14 may sense atrial systolic events by sensing atrial P-waves that are attendant to atrial depolarizations. P-waves are relatively low amplitude signals in the near-field RV electrical signal received by pacemaker 14 (e.g., compared to the near-field R-waves) and therefore can be difficult to consistently detect from the cardiac electrical signal acquired by pacemaker 14 implanted in a ventricular chamber. Atrial-synchronized ventricular pacing by pacemaker 14 may not be reliable when based solely on a cardiac electrical signal received by pacemaker 14. According to the techniques disclosed herein, the pacemaker 14 may include a motion sensor, such as an accelerometer, and may be configured to detect an atrial event corresponding to atrial mechanical activation or atrial systole using a signal from the motion sensor. However, it is contemplated that other types of sensors of cardiac mechanical or hemodynamic function may be used to produce a cardiac mechanical signal and sense atrial systolic events from the cardiac mechanical signal. Such sensors may include impedance sensors (which produce a signal correlated to blood volume in the ventricle), pressure sensors, acoustical sensors or other sensors that produce a signal correlated to the mechanical contractions of the heart chambers.

Ventricular pacing pulses are synchronized to the atrial event, which may be detected from the accelerometer signal as described below, by setting a programmable atrioventricular (AV) pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event and/or set sensing parameters used for discriminating the atrial systolic event from other cardiac motion events.

A target AV interval may be a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by pacemaker 14 and the motion sensor signal received by pacemaker 14. The AV interval may be set to about 10 to 200 ms, in some examples, to control pacemaker 14 to deliver a ventricular pacing pulse synchronized to the atrial event sensed from the motion signal.

Pacemaker 14 may be capable of bidirectional wireless communication with an external device 20 for programming the AV pacing interval and other pacing control parameters as well as both electrical and mechanical event sensing parameters utilized for detecting ventricular events and the atrial systolic events from the cardiac electrical signal and/or motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 is configured for bidirectional communication with implantable telemetry circuitry included in pacemaker 14. External device 20 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link.

External device 20 may display data and information relating to pacemaker functions to a user for reviewing pacemaker operation and programmed parameters as well as EGM signals transmitted from pacemaker 14, motion sensor signals acquired by pacemaker 14, or other physiological data that is acquired by and retrieved from pacemaker 14 during an interrogation session.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in pacemaker 14, e.g., after viewing a visual representation of EGM, motion sensor signal and marker channel data.

Figure 2A:
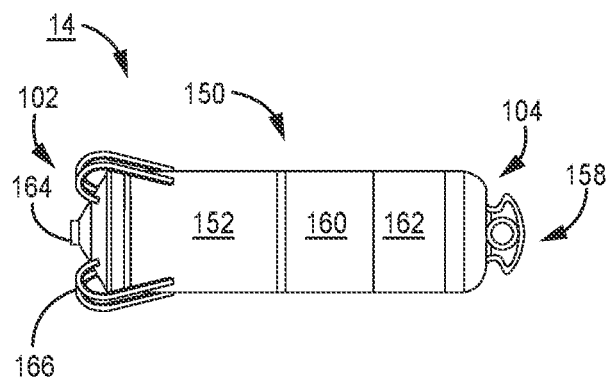
FIG. 2A is a conceptual diagram of the intracardiac pacemaker shown in FIG. 1.

FIG. 2A is a conceptual diagram of the intracardiac pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,872 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 2B:
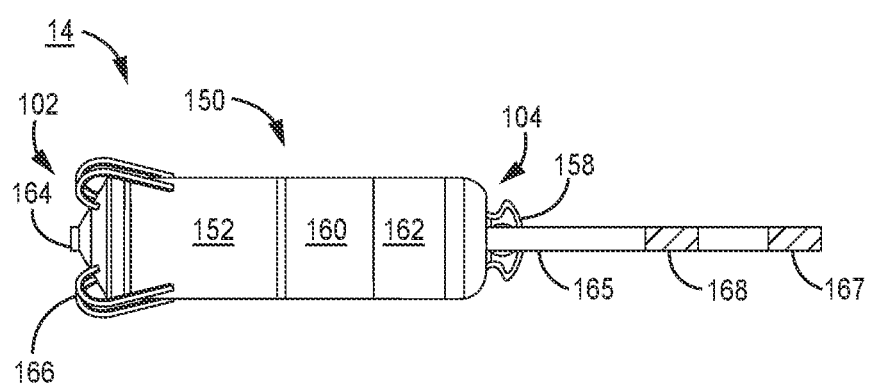
FIG. 2B is a conceptual diagram of another example of the pacemaker of FIG. 1.

FIG. 2B is a conceptual diagram of another example of pacemaker 14. In FIG. 2B, pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field signals which may include atrial P-waves attendant to atrial depolarizations.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
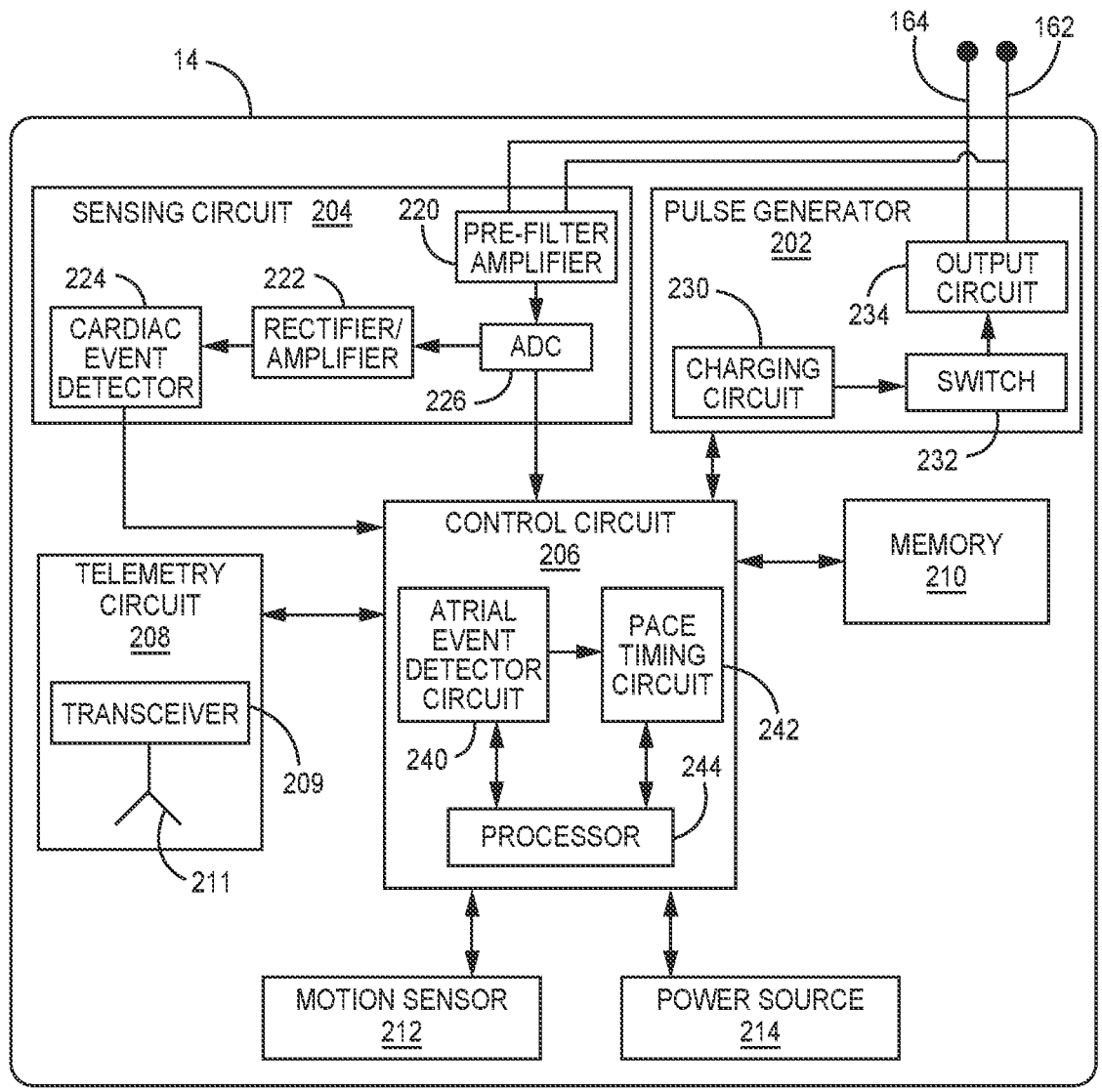
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors or mechanical sensors may be utilized successfully in pacemaker 14 for detecting cardiac motion signals according to the techniques described herein. Examples of motion sensors that may be implemented in motion sensor 212 include piezoelectric sensors and MEMS devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. The motion sensor 212 may include filters, amplifiers, rectifiers, an ADC and/or other components for producing a motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

Cardiac event detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the cardiac event detector 224 produces an R-wave sensed event signal (R-sense) that is passed to control circuit 206. In other examples, cardiac event detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

In some examples, cardiac event detector 224 is configured to sense P-waves from the cardiac electrical signal received by electrodes 162 and 164 (and/or electrodes carried by a sensing extension, such as extension 165 shown in FIG. 2B). Cardiac event detector 224 may compare the incoming signal to a P-wave sensing threshold and produce a P-wave sensed event signal passed to control circuit 206 in response to a threshold crossing. When pacemaker 14 is configured to sense R-waves and P-waves, sensing circuit 204 may include two different sensing channels, each including a pre-filter/amplifier, ADC, rectifier/amplifier and cardiac event detector configured to amplify and filter cardiac electrical signals received via one or two different sensing electrode pairs for separately sensing R-waves and P-waves from the cardiac electrical signals. P-wave sensing may be used for verifying atrial events sensed from a motion sensor signal or vice versa. In some examples, P-wave sensed event signals are used by control circuit 206 for starting an AV interval for controlling atrial synchronized ventricular pacing pulses delivered by pulse generator 202.

Control circuit 206 includes an atrial event detector circuit 240, pace timing circuit 242, and processor 244. Atrial event detector circuit 240 is configured to detect atrial mechanical events from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals, P-wave sensed event signals, and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking (asynchronous) ventricular pacing mode. R-wave sensed event signals may also be passed to atrial event detector circuit 240 for use in setting time windows used by control circuit 206 for detecting atrial systolic events from the motion sensor signal.

Atrial event detector circuit 240 receives a motion signal from motion sensor 212 and may start an atrial refractory period in response to a ventricular electrical event, e.g., an R-wave sensed event signal from sensing circuit 204 or delivery of a ventricular pacing pulse by pulse generator 202. In some examples, atrial event detector circuit 240 determines if the motion sensor signal satisfies atrial mechanical event detection criteria outside of the refractory period. The motion sensor signal during the refractory period may be monitored by atrial event detector circuit 240 for the purposes of detecting ventricular mechanical events, which may be used for confirming or validating atrial systolic event detection. As such, ventricular mechanical event detection windows may be set during the atrial refractory period and may be set according to predetermined time intervals following identification of a ventricular electrical event. Atrial event detector circuit 240 may be configured to detect one or more ventricular mechanical events during respective ventricular event detection windows, during the atrial refractory period. The timing and detection of the ventricular mechanical events may be used to update the atrial refractory period and/or an atrial systolic detection threshold amplitude and may be used to confirm detection of the atrial systolic event occurring subsequent to expected ventricular mechanical events.

Atrial event detector circuit 240 may set time windows corresponding to the passive ventricular filling phase and the active ventricular filling phase based on the timing of a preceding ventricular electrical event, either an R-wave sensed event signal or a ventricular pacing pulse. A motion sensor signal crossing of an atrial event detection threshold during either of these windows may be detected as the atrial systolic event. As described below, two different atrial event detection thresholds may be established for applying during the respective passive filling phase window and active filling phase windows.

Atrial event detector circuit 240 passes an atrial event detection signal to processor 244 and/or pace timing circuit 242 in response to detecting an atrial systolic event from the motion sensor signal. In other examples, the atrial systolic event may be detected as a mechanical event from the motion sensor signal and/or as the electrical event (P-wave) by sensing circuit 204. A P-wave sensed event signal may be passed from cardiac event detector 224 to atrial event detector circuit 240 or directly to pace timing circuit 242. In still other examples, pacemaker 14 may be configured to receive a signal, e.g., via telemetry circuit 208, from another medical device indicating the timing of the atrial systolic event. Another medical device may be an intra-atrial pacemaker or a subcutaneously or submuscularly implanted sensing device, pacemaker or implantable cardioverter defibrillator configured to sense P-waves and transmit or broadcast a signal to pacemaker 14 to indicate the timing of a sensed P-wave or delivered atrial pacing pulse. Other examples of atrial event sensing or detection for use in controlling atrial synchronized ventricular pacing by an intracardiac ventricular pacemaker are generally disclosed in U.S. Pat. Publication No. 2018/0161580 A1 (Demmer, et al) and in U.S. Publication No. 2016/0144190 (Cao, et al.), both of which are incorporated herein by reference in their entirety.

Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Pace timing circuit 242 may additionally include a lower pacing rate interval timer for controlling a lower ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate. As described below, in order to avoid abrupt changes in ventricular rate and promote atrial event sensing recovery when an atrial event is not sensed during a cardiac cycle, control circuit 206 may be configured to set a ventricular pacing interval to a rate smoothing interval during an atrial tracking ventricular pacing mode. The rate smoothing interval may be determined based on one or more preceding ventricular event intervals. For example, the actual pacing rate intervals between consecutively delivered ventricular pacing pulses (Vp-Vp intervals) may be determined. The Vp-Vp intervals may be determined as the interval between two consecutively delivered pacing pulses or between the corresponding two consecutive evoked R-waves sensed from the cardiac electrical signal by sensing circuit 204. A rate smoothing interval may be set based on the actual Vp-Vp intervals so that a ventricular pacing pulse delivered in the absence of a sensed atrial event is delivered at an interval that is within a predetermined interval of preceding Vp-Vp intervals, e.g., within 150 ms or within 100 ms.

At times, control circuit 206 may control pulse generator 202 in a non-atrial tracking ventricular pacing modes (also referred to as "asynchronous ventricular pacing") during which a VV interval may be set based on a patient activity metric determined from motion sensor 212 or according to a programmed lower rate. If control circuit 206 switches from an atrial-tracking ventricular pacing mode to a non-atrial tracking ventricular pacing mode, control circuit 206 may set rate smoothing intervals to control a gradual adjustment of the ventricular pacing rate from the atrial tracking Vp-Vp intervals to a ventricular lower rate used to control the ventricular pacing rate during the non-atrial tracking pacing mode, e.g., a VVI or VDI pacing mode.

Processor 244 may retrieve other programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, processor 244 may provide sensing control signals to sensing circuit 204, e.g., R-wave sensing threshold, P-wave sensing threshold, sensitivity, and/or various blanking and refractory intervals applied to the cardiac electrical signal.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval, a VV rate smoothing interval, or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Memory 210 may store one or more Vp-Vp intervals for determining a rate smoothing interval, In some examples, the most recent Vp-Vp interval is determined as an actual ventricular pacing rate. In other examples, memory 210 may buffer a series of ventricular event intervals, e.g., Vp-Vp intervals (or evoked RR intervals), for determining an actual ventricular pacing rate as the mean or median Vp-Vp interval that is used by processor 244 for determining a VV rate smoothing pacing interval. For instance, pace timing circuit 242 may include a timer or counter that is started upon delivery of a ventricular pacing pulse and is used to determine the Vp-Vp time interval until the next delivered ventricular pacing pulse. The Vp-Vp time interval may be stored in memory 210, e.g., in a first-in-first-out buffer of a predetermined number of Vp-Vp time intervals. In one example, up to 12 Vp-Vp intervals are stored for determining a median Vp-Vp interval, though more than or less than 12 Vp-Vp intervals may be stored for determining a mean or median Vp-Vp interval.

Processor 244 may be configured to set a VV rate smoothing interval to a predetermined increment greater than the actual ventricular pacing rate, which may be determined based on a single most recent Vp-Vp interval or a median or mean of multiple Vp-Vp intervals in some examples. The predetermined increment may be set to 10 ms, 25 ms, 50 ms, 75 ms, 100 ms, 150 ms, or other selected time interval. Processor 244 may control pace timing circuit 242 to start a VV pacing interval timer or counter to time out the VV rate smoothing interval. If the VV rate smoothing interval expires without an atrial systolic event being sensed, a ventricular pacing pulse is delivered at the rate smoothing interval by pulse generator 202.

Power source 214 provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed, power to transceiver 209, motion sensor 212, and ADC 226 and other circuitry of sensing circuit 204 as needed as well as memory 210.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 4:
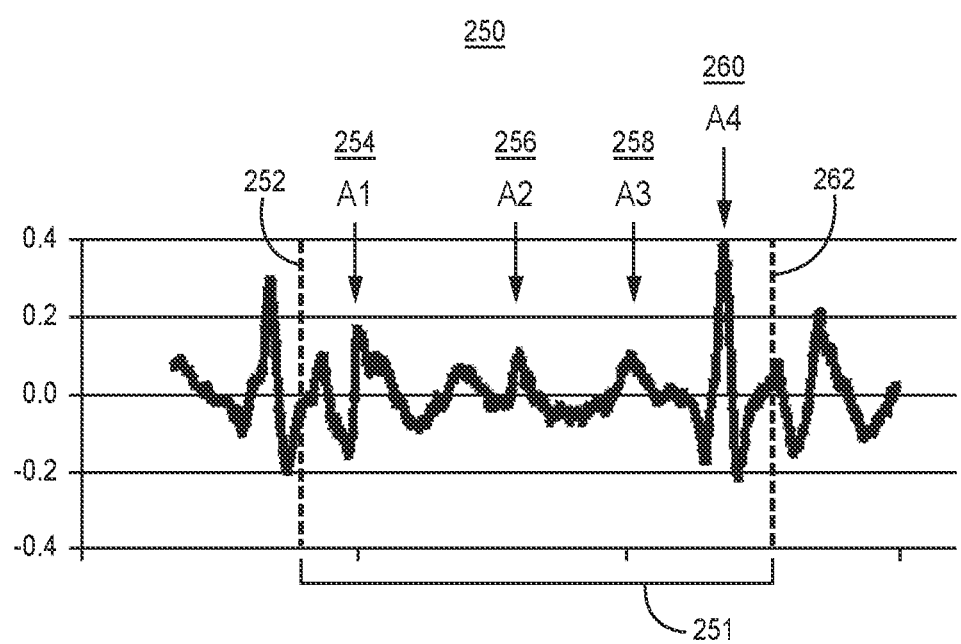
FIG. 4 is an example of a motion sensor signal that may be acquired by an intracardiac pacemaker over a cardiac cycle.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A1 event is also referred to herein as a "ventricular contraction event." The A2 event 265 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 may also referred to herein as the "atrial systolic event" or merely the "atrial event," and is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260. As described below, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
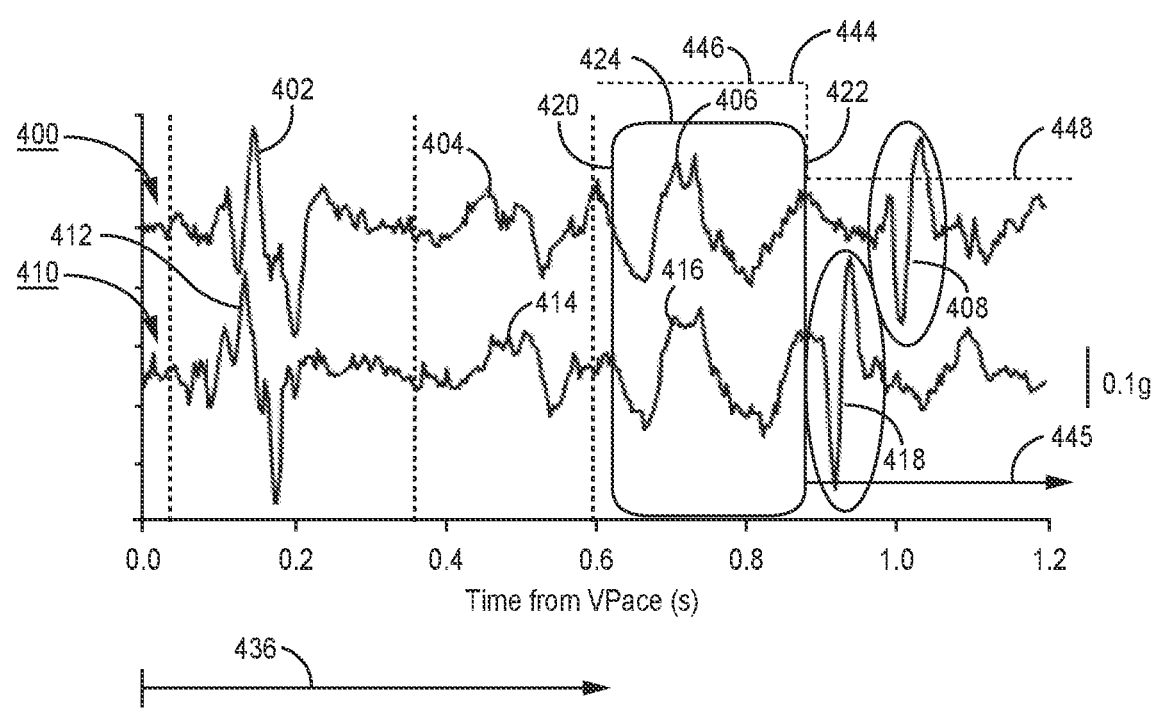
FIG. 5 is an example of motion sensor signals acquired over two different cardiac cycles.

FIG. 5 is an example of motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that control circuit 206 may receive a filtered, amplified and rectified signal from motion sensor 212 for processing and analysis as described in conjunction with the flow charts and histogram distributions presented herein.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring during ventricular relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of A1, A2 and A3 events to each other and the immediately preceding ventricular electrical event is expected to be consistent.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining an atrial refractory period 436 and increasing confidence in reliably detecting A4 events 408 and 418. The atrial systolic event is not detected during the atrial refractory period 436 which extends from the ventricular electrical event (at time 0.0) to an estimated onset of ventricular systole. An A3 sensing window 424 may be set having a starting time 420 corresponding to the end of the post-ventricular atrial refractory period 436 and an ending time 422.

A4 events 408 and 418 may be detected based on a multi-level A4 detection threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 threshold amplitude 446 may be established for detecting an early A4 event that is fused with the A3 event during the A3 window 424. A second, lower A4 threshold amplitude 448 may be established for detecting relatively later A4 events, after the ending time 422 of the A3 window 424. The earliest crossing of the A4 detection threshold 444 by the motion sensor signal after the starting time 420 of the A3 window (or after the expiration of the atrial refractory period 436) may be detected as the atrial systolic event. Various examples of an intracardiac pacemaker configured to detect atrial systolic events from a motion sensor signal for delivering atrial synchronized ventricular pacing are disclosed in commonly assigned U.S. Pat. Publication No. 2018/0085589 (Splett et al.), U.S. Pat. Publication No. 2018/0085588 (Splett, et al.), U.S. Pat. Publication No. 2018/0117337 (Demmer, et al.), U.S. Pat. Publication No. 2018/0161580 (Demmer, et al.) and U.S. Pat. No. 10,207,116 (Sheldon, et al.), all of which are incorporated herein by reference in their entirety. The techniques disclosed herein for controlling the timing of ventricular pacing pulses using rate smoothing pacing intervals may be implemented in any of the examples presented in the foregoing incorporated references.

Figure 6:
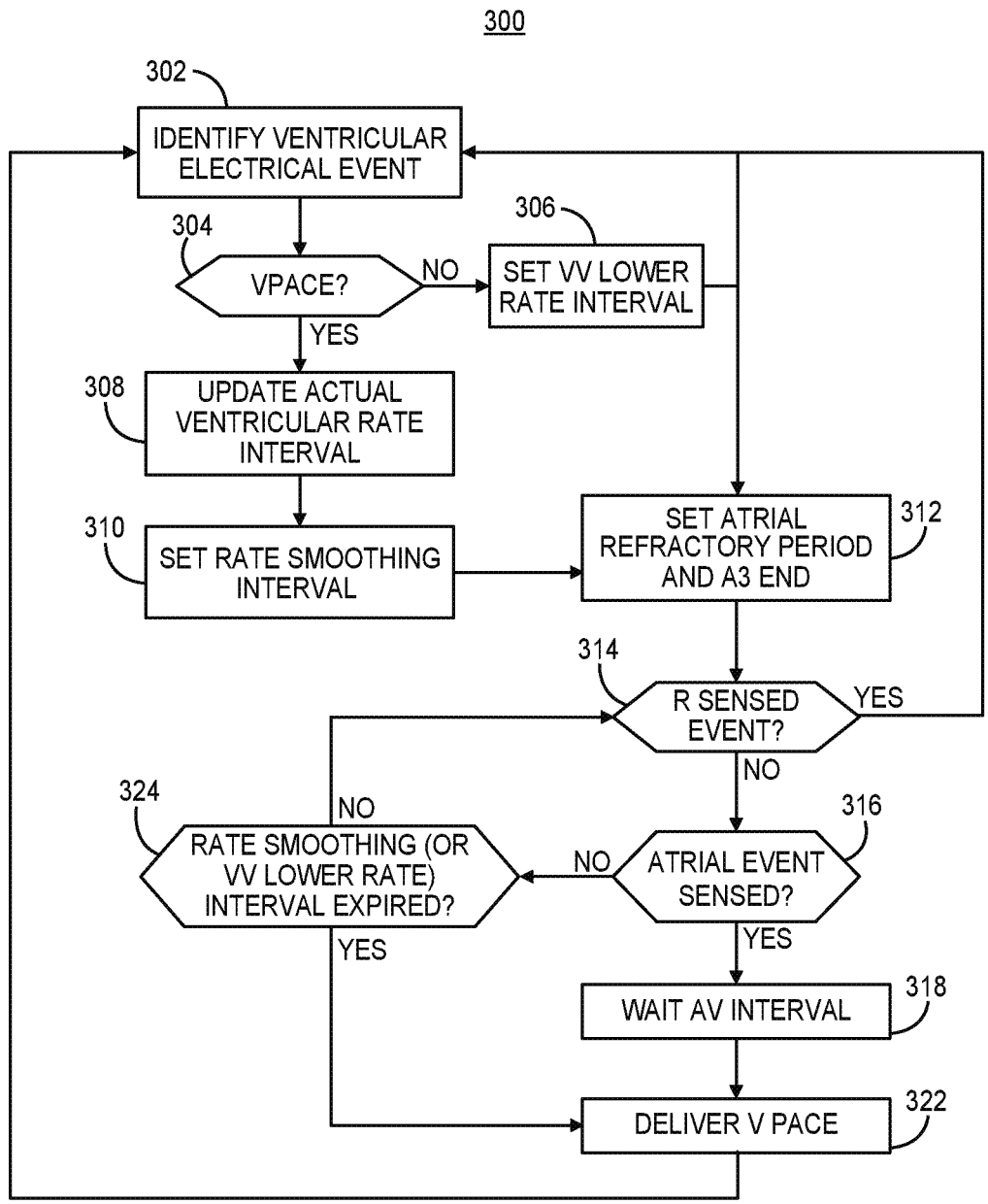
FIG. 6 is a flow chart of a method for controlling ventricular pacing pulses delivered by a ventricular pacemaker, such as the intracardiac ventricular pacemaker of FIG. 1, according to one example.

FIG. 6 is a flow chart 300 of a method for controlling ventricular pacing pulses delivered by a ventricular pacemaker, such as intracardiac ventricular pacemaker 14, according to one example. At block 302, control circuit 206 identifies a ventricular electrical event. The ventricular event may be a sensed intrinsic R-wave, e.g., when control circuit 206 receives an R-wave sensed event signal from sensing circuit 204. In this case, control circuit 206 starts a VV lower rate pacing interval (block 306). Generally, atrial synchronized ventricular pacing is being delivered in a patient having AV block. Atrial depolarizations are either not conducted or may be conducted at a very long delay. Some patients having some degree of AV block may experience episodes of AV conduction and/or premature ventricular contractions (PVCs). If a sensed intrinsic ventricular event occurs, control circuit 206 sets a VV pacing interval to the lower rate interval, e.g., 1.5 to 1.0 second corresponding to a lower rate of 40 to 60 pulses per minute. In this way, a relatively long pacing interval promotes sensing of the next atrial event during the long pacing interval.

If the ventricular electrical event identified at block 302 is a ventricular pacing pulse (Vpace) delivered by pulse generator 202 (or subsequent evoked R-wave sensed by sensing circuit 204), control circuit 206 may update an actual ventricular pacing rate interval at block 308. The actual ventricular pacing rate may be the most recent, preceding Vp-Vp interval (or sensed R-wave to Vpace interval), which may or may not include an intervening sensed A4 event. In another example, a median Vp-Vp interval is determined as the median of the most recent twelve Vp-Vp intervals. Each Vp-Vp interval is the time interval between a pair of consecutively delivered ventricular pacing pulses (or corresponding evoked R-waves). Sensed intrinsic ventricular R-waves may be ignored for determining the Vp-Vp intervals in some examples. Since the patient may have AV block, any intrinsically sensed R-wave may be a PVC. The short interval preceding the PVC and the long interval following a PVC may be ignored because they are not representative of the regular ventricular rate. In other examples, all ventricular event intervals, including both sensed and paced intervals, may be used in updating a ventricular rate interval at block 308. PVCs may be identified based on short-long intervals and/or morphology difference from normally conducted R-waves and excluded from updating an actual ventricular event interval at block 308, while other intrinsically sensed R-waves that appear to be conducted from the atrium may be used in determining ventricular event intervals used in updating the actual ventricular rate interval.

Control circuit 206 uses the actual ventricular rate interval updated at block 308 (or updated on a preceding ventricular paced event) for setting a rate smoothing interval at block 310 in response to the delivered ventricular pacing pulse. The rate smoothing interval is a VV pacing interval that is used to control the timing of the next ventricular pacing pulse in the absence of a sensed atrial event. As described below, instead of delivering a ventricular pacing pulse at a programmed lower rate interval following every Vpace when an atrial event is not sensed, the rate smoothing interval allows ventricular pacing to occur near an expected atrial rate based on the preceding actual, atrial-tracking ventricular pacing rate. The rate smoothing interval avoids an abrupt ventricular rate change and preserves the timing of the post-ventricular atrial refractory period and the start and end of the A3 window relative to a preceding ventricular pacing pulse to promote a rapid return to atrial sensing.

In some examples, the rate smoothing interval is started only in response to a delivered ventricular pacing pulse, which may follow a sensed A4 event at an AV interval or a ventricular pacing pulse delivered at the lower rate interval or the rate smoothing interval. When an intrinsic R-wave is sensed, control circuit 206 may start only the programmed lower rate interval without applying the rate smoothing interval. In other examples, the rate smoothing interval may be started in response to a sensed, intrinsic R-wave. For instance, when the sensed intrinsic R-wave occurs at a ventricular event rate interval near the expected atrial rate, a rate smoothing interval may be started in response to the sensed intrinsic R-wave.

Along with starting either the VV lower rate interval at block 306 in response to an intrinsic ventricular sensed event or the rate smoothing interval at block 310 in response to a ventricular pacing pulse, control circuit 206 starts a post-ventricular atrial refractory period at block 312. Any event sensed during the post-ventricular atrial refractory period is not used to start an AV pacing interval. Upon expiration of the atrial refractory period, control circuit 206 may start an A3 (passive ventricular filling) window that is terminated at according to an A3 window end time, e.g., as shown in FIG. 5.

If an R-wave is sensed before the rate smoothing or VV lower rate interval expires, as determined at block 314, control circuit 206 returns to block 302. The scheduled pacing pulse is withheld, and the VV lower rate interval may be restarted at block 306. Some patients may experience a run of PVCs which are not used for updating the actual ventricular rate interval. In other cases, R-wave sensing may indicate a return of AV conduction.

As long as an R-wave is not sensed at block 314, control circuit 206 waits for an atrial event to be sensed at block 316. If an atrial event is not sensed ("no" branch of block 316), the rate smoothing interval (or the VV lower rate interval) continues to run (block 324). If an atrial event is sensed at block 316, control circuit 206 responds by starting the AV interval at block 318. The atrial event may be sensed from the motion sensor signal in response to an A4 threshold crossing. As described above, a higher A4 threshold crossing may be applied during the A3 window and a lower A4 threshold may be applied starting from the end of the A3 window until either an A4 event is sensed or a ventricular pacing pulse is delivered (or intrinsic R-wave sensed). In other examples, the atrial event may be a P-wave sensed from a cardiac electrical signal. In still other examples, the atrial event sensed at block 316 may be a communication signal or trigger signal transmitted by another co-implanted medical device and received by pacemaker 14 to indicate that an atrial P-wave or atrial pacing pulse has occurred.

At block 322, control circuit 206 delivers a ventricular pacing pulse upon expiration of the AV interval. The rate smoothing interval is canceled and a ventricular pacing pulse scheduled at the expiration of the rate smoothing interval is withheld. Control circuit 206 returns to block 302 and updates the actual ventricular rate interval at block 308 using the most recent Vp-Vp interval. It is to be understood that in some examples, an R-wave may be sensed during the AV interval at block 318, in which case the AV interval may be suspended the corresponding scheduled ventricular pacing pulse may be withheld. In this case, the process returns to block 302 without delivering an atrial synchronized ventricular pacing pulse.

If an atrial event is not sensed ("no" branch of block 316) and the rate smoothing interval (or the VV lower rate interval) expires at block 324, a ventricular pacing pulse is delivered at the rate smoothing interval (or the VV lower rate interval). When a ventricular pacing pulse is delivered at the rate smoothing interval from a preceding ventricular pacing pulse, the rate smoothing interval will be used to update the actual pacing rate interval at block 308. The actual pacing rate may be updated to equal the single, preceding Vp-Vp interval or determined from multiple preceding Vp-Vp intervals, e.g., as a mean or median value. If multiple ventricular pacing pulses are delivered at rate smoothing intervals on consecutive cycles without atrial sensed events or at increasing Vp-Vp intervals that include atrial sensed events (with Vpaces delivered at the AV interval), the rate smoothing intervals will gradually increase since each rate smoothing interval is based on the updated actual pacing rate interval plus a predetermined increment, e.g., 8 to 200 ms. If atrial sensing is lost for multiple cardiac cycles, the rate smoothing interval gradually increases and approaches the VV lower rate interval. If the VV lower rate interval is reached, the rate smoothing interval set in response to a ventricular pacing pulse is not set to be greater than the VV lower rate interval. In other words, the maximum rate smoothing interval may be equal to the VV lower rate interval.

Figure 7:
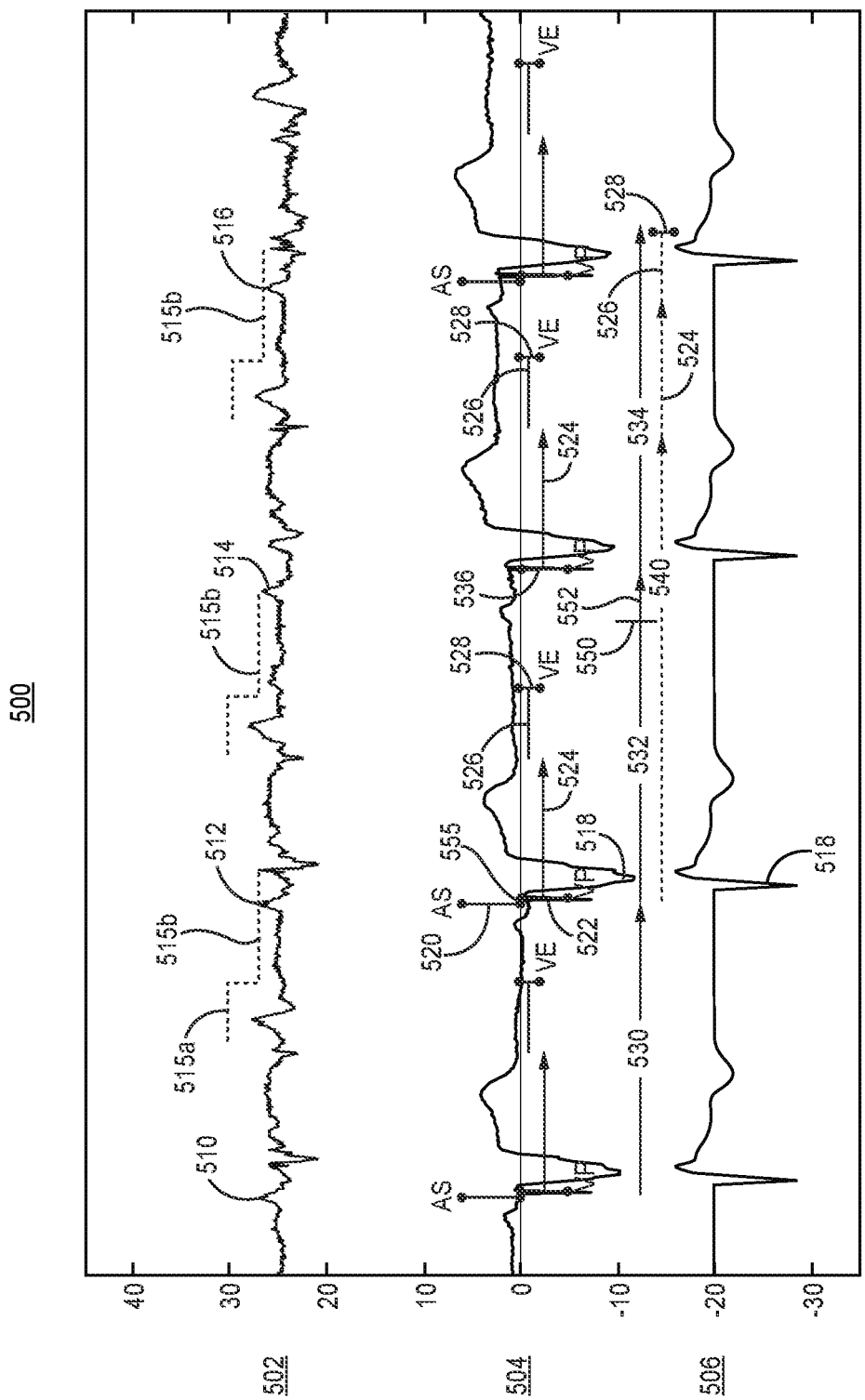
FIG. 7 is a diagram of a motion sensor signal, electrocardiogram signal and marker channel, and ventricular EGM signal depicting the rate smoothing ventricular pacing techniques disclosed herein.

FIG. 7 is a diagram 500 of a motion sensor signal 502, electrocardiogram signal and marker channel 504, and ventricular EGM signal 506. Motion sensor signal 502 is shown as a non-rectified signal in the example of FIG. 7, however it is to be understood that the motion sensor signal 502 may be filtered and rectified for sensing A4 signals representative of atrial mechanical systole. Motion sensor signal 502 includes A4 signals 510, 512, 514 and 516. An early A4 sensing threshold 515a may be applied during an A3 window 526, and a late A4 sensing threshold 515b may be applied to motion sensor signal 502 after the A3 window end 528. The early and late A4 sensing thresholds 515a and 515b are referred to collectively as the A4 sensing threshold 515. A4 signals 510, 512 and 516 each cross the A4 sensing threshold 515 resulting in a respective atrial sensed event signal 520 shown on ECG and marker channel signal 504. A4 signal 514 does not cross the A4 sensing threshold 515 and is not sensed by the atrial event detector circuit 240.

ECG and marker channel signal 504 shows a ventricular pacing pulse 522 delivered in response to each atrial sensed event signal 520. Control circuit 206 sets an AV interval 555, e.g., as short as 10 ms, in response to atrial event detector circuit 240 producing an atrial sensed event signal 520. Pulse generator 202 delivers the ventricular pacing pulse 522 upon expiration of the AV interval, causing an evoked R-wave 518 on both the ECG signal (504) and the ventricular EGM signal 506. In response to delivering a ventricular pacing pulse 522, the actual pacing interval 530 between the current and immediately preceding pacing pulse is used to update an actual ventricular rate interval. The actual ventricular rate interval may be set to the current Vp-Vp interval 530, set to the current Vp-Vp interval plus or minus an adjustment interval for tracking a trend in the Vp-Vp intervals, or set to an actual rate interval determined from multiple Vp-Vp intervals, e.g., as the median of 12 (or other predetermined number) of consecutive Vp-Vp intervals. It is to be understood that the consecutive Vp-Vp intervals used to update the actual pacing rate interval may not represent consecutive ventricular event intervals since an intervening PVC or intrinsically conducted R-wave may occur. A cardiac cycle interval beginning or ending with a sensed intrinsic R-wave may be ignored for the purposes of updating the actual ventricular rate interval. The actual ventricular rate interval updated upon delivering the ventricular pacing pulse 522 (or the immediately preceding updated actual ventricular rate interval) is used by control circuit 206 to set a rate smoothing interval 532. The rate smoothing interval may be set an increment 552, e.g., 100 ms, longer than the updated actual ventricular rate interval 550, as an example.

In response to delivery of the ventricular pacing pulse 522, control circuit 206 sets a post-ventricular atrial refractory period 524 followed by A3 window 526 which is terminated at A3 window end 528. The rate smoothing interval 532 expires due to undersensing of the A4 signal

514. Control circuit 206 controls pulse generator 202 to deliver a ventricular pacing pulse 536 upon expiration of rate smoothing interval 532, which starts another atrial refractory period 524 followed by A3 window 526. The ventricular pacing pulse 536 is delivered near the actual ventricular rate interval that was previously tracking the atrial rate (e.g., the rate of sensed A4 signals 510 and 512). As such, the next atrial event, in this case A4 signal 516, is expected to be outside the atrial refractory period 524 and may be after the next A3 window end 528. By delivering the ventricular pacing pulse 536 at the rate smoothing interval set based on the actual ventricular rate interval instead of at the VV lower rate interval, the likelihood of sensing the next A4 signal 516 during or after the A3 window 526 is increased.

This improvement in the increased likelihood of sensing an A4 signal following a ventricular pacing pulse delivered at a rate smoothing interval is demonstrated by the dashed VV lower rate interval 540. If the VV lower rate interval 540 is started in response to ventricular pacing pulse 522, the next ventricular pacing pulse would be delivered much later in the atrial cycle, potentially precluding or interfering with atrial event sensing. If a pacing pulse were delivered at the expiration of VV lower rate interval 540, a subsequent atrial refractory period 524 (shown by dashed line) and A3 window end 528 occur much later in time. The next atrial event 516 may occur after the VV lower rate interval 540 during the post-ventricular atrial refractory period 524 (and go undetected) or during the A3 window 526 but be too small to be detected. Several cycles of ventricular pacing pulses may be delivered at the VV lower rate interval 540 before an atrial event is sensed outside the atrial refractory period 524. The timing of the A3 window end 528 is substantially preserved relative to actual atrial rate by setting the rate smoothing interval 532 based on an actual ventricular rate interval, thereby promoting a rapid return to A4 sensing, as early as the next cardiac cycle (A4 event 516) in this example. In this way, the percentage of ventricular pacing pulses that are delivered synchronously with atrial systolic events may be increased by using a rate smoothing interval based on the actual ventricular rate interval for controlling the timing of a ventricular pacing pulse in the absence of an atrial sensed event. Atrial event sensing is quickly regained after a single cycle or sporadic or intermittent atrial event undersensing.

Figure 8:
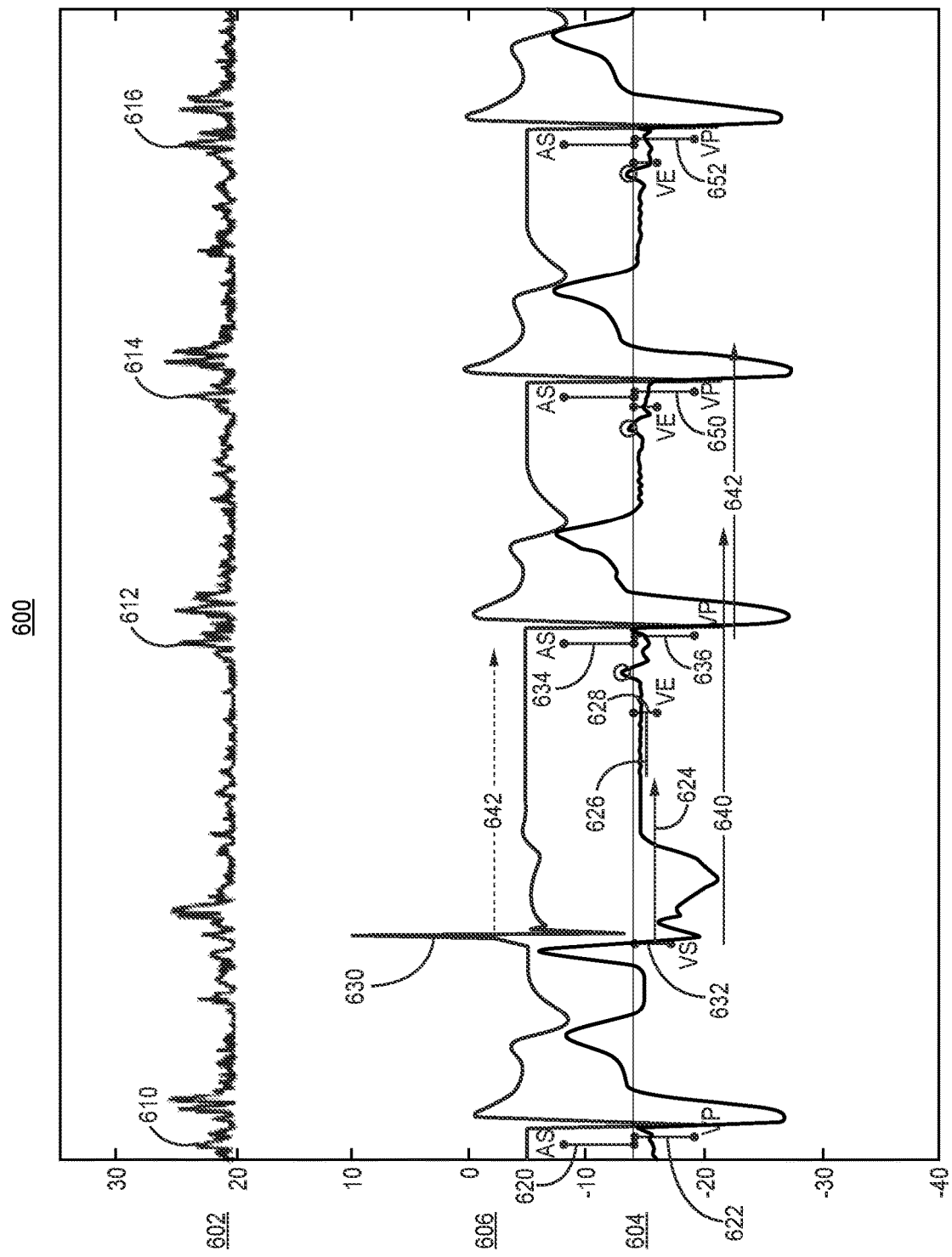
FIG. 8 is a diagram of a motion sensor signal, ECG signal and marker channel, and ventricular EGM signal including a premature ventricular contraction.

FIG. 8 is a diagram 600 of a motion sensor signal 602, an ECG signal and marker channel 604, and a ventricular EGM signal 606 including a PVC 630. Motion sensor signal 602 is a rectified signal including A4 signals 610, 612, 614 and 616. A4 signal 610 is sensed by control circuit 206, and an atrial sensed event signal 620 is produced. In response to the A4 sensed event signal 620, control circuit 206 delivers a ventricular pacing pulse 622 after an AV interval (which may be as short as 10 ms and is therefore not shown in FIG. 8 but is to be understood as being the time interval between the atrial sensed event signal 620 and ventricular pacing pulse 622). In response to delivering the ventricular pacing pulse 622, control circuit 206 may set an atrial refractory period followed by an A3 window as described above in conjunction with FIGS. 6 and 7. Control circuit 206 may update an actual ventricular rate interval and set a rate smoothing interval based on the actual ventricular rate interval as described above in conjunction with FIGS. 6 and 7.

In the example of FIG. 8, a PVC 630 occurs prior to the end of the A3 window following ventricular pacing pulse 622. The PVC 630 is sensed by sensing circuit 204. An R-wave sensed event signal 632 is produced and passed to control circuit 206. The PVC interferes with A4 event sensing due to ventricular event motion signals present in the motion sensor signal 602 around the time of the A4 signal and/or the PVC preceding the A3 window end and causing a post-ventricular atrial refractory period to be started.

The ventricular event interval starting with ventricular pacing pulse 622 and ending with ventricular sensed event 632 is not used to update the actual ventricular rate interval in some examples. Control circuit 206 does not start a rate smoothing interval in response to the ventricular sensed event signal 632. Instead, the VV lower rate interval 640 is started in response to the ventricular sensed event signal 632. Since a sensed event may be a PVC in a patient with AV block, a long pause is expected to follow the PVC. If the rate smoothing interval 642 (shown by dashed line) set based on a previously updated actual ventricular rate interval were started in response to the ventricular sensed event signal 632, the rate smoothing interval 642 may expire prior to the next atrial cycle causing a pacing pulse before next expected atrial event 612. As such, rate smoothing is withheld in response to an intrinsic ventricular sensed event to promote sensing of the next atrial event 612 without interference of a ventricular pacing pulse.

In response to ventricular sensed event signal 632, the atrial refractory period 624 is started and is followed by the A3 window 626. The next atrial event 612 is sensed after the A3 window end 628, before expiration of the relatively long VV lower rate interval 640. The ventricular pacing pulse scheduled to occur at the expiration of the VV lower rate interval 640 is withheld or canceled. Instead, a ventricular pacing pulse 636 is delivered after an AV interval started in response to the atrial sensed event signal 634. In this way, atrial synchronized ventricular pacing is regained on the next atrial event following a PVC in this example.

The ventricular event interval ending with ventricular pacing pulse 636 may not be used to update the actual ventricular rate interval since the ventricular event interval is started by the intrinsic ventricular sensed event 632 and does not reflect a true atrial synchronized ventricular event interval. The most recently determined rate smoothing interval 642, based on the most recently updated actual ventricular rate interval using only Vp-Vp intervals, may be started in response to the delivered ventricular pacing pulse 636. This rate smoothing interval 642 does not expire before the next A4 signal 614 is sensed, promoting delivery of atrial synchronized ventricular pacing pulses 650, 652, each delivered in response to sensed atrial events 614 and 616, respectively.

In a ventricular pacing system in which atrial event signals have a relatively low or variable amplitude, applying a rate smoothing interval following ventricular pacing pulses and withholding the rate smoothing interval following intrinsic ventricular sensed events (and applying the lower rate pacing interval instead) promotes recovery of atrial event sensing following atrial event undersensing. The rate smoothing techniques disclosed herein may be implemented in a variety of ventricular pacing systems and are particularly useful in ventricular pacing systems that include a sensor, such as a motion sensor or electrodes, for sensing atrial events from a signal that is acquired within the ventricular chamber. Atrial event signals in a cardiac signal acquired within the ventricular chamber will have relatively low signal-to-noise ratio compared to ventricular event signals.

Figure 9:
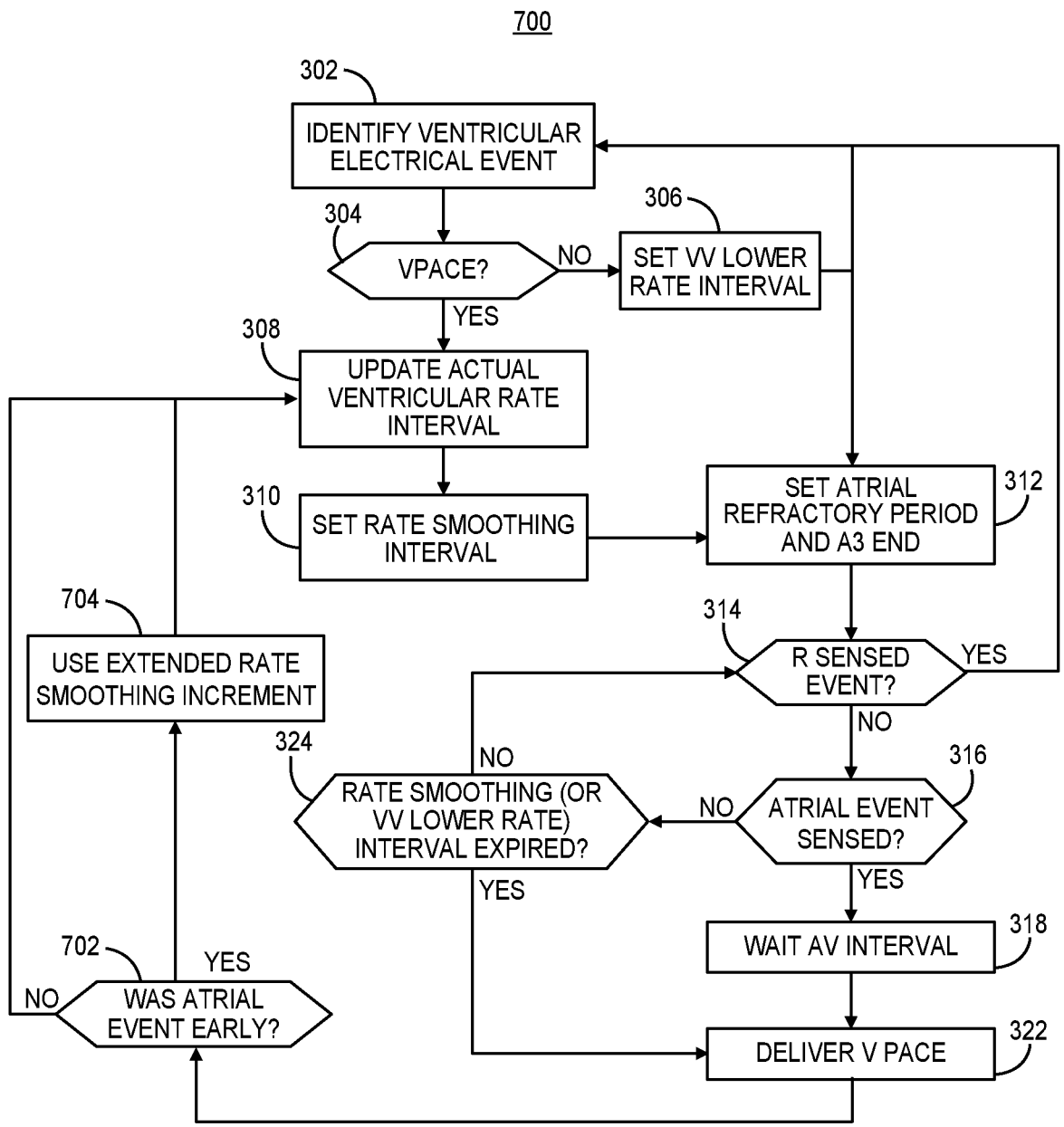
FIG. 9 is a flow chart of a method that may be performed by a pacemaker according to another example.

FIG. 9 is a flow chart 700 of a method that may be performed by pacemaker 14 according to another example.

Identically-numbered blocks in FIG. 9 correspond to like-numbered blocks shown in FIG. 6 and are described above in conjunction with FIG. 6. In the example of FIG. 9, control circuit 206 is configured to determine if a sensed atrial event that triggers delivery of a ventricular pacing pulse at block 322 is an early atrial event at block 702. An early atrial event may be detected based on sensing the atrial event within a threshold time interval after the preceding ventricular pacing pulse (or sensed R-wave). In one example, an early atrial event is before 50 ms after the A3 window end, though other criteria for detecting an early atrial event may be defined. An early atrial event, e.g., early after the A3 window end or during the A3 window, may be a premature atrial contraction (PAC). A PAC produces a short atrial cycle followed by a long atrial cycle corresponding to the compensatory pause that generally follows a PAC.

As such, in order to promote sensing of the next atrial event ending the long pause, control circuit 206 may adjust the rate smoothing increment to an extended increment at block 704 in response to identifying a sensed atrial event at an early event at block 702. The extended increment is used for setting an extended rate smoothing interval at block 310, which is started following the ventricular pacing pulse delivered at an AV interval after the early atrial sensed event.

In other examples, oversensing may cause a false detection of an atrial systolic event. For instance, the A3 event (see FIG. 4) corresponding to the passive ventricular filling phase may be detected as an A4 event if it occurs after the A3 window and crosses the A4 sensing threshold. The A3 event generally occurs earlier after a ventricular pacing pulse than an A4 event (given a relatively stable atrial rate) so that an early atrial sensed event may be an indication of an oversensed A3 event. By extending the rate smoothing interval by a longer increment following an early atrial sensed event, the time for sensing the true A4 event on the next cycle is not prematurely terminated by a rate smoothing interval that is started early, following a ventricular pacing pulse synchronized to the early atrial sensed event. If the early event is an oversensed A3 event, A4 event sensing may be regained on the next cardiac cycle, during the extended rate smoothing interval, thereby returning to appropriate atrial synchrony of ventricular pacing pulses.

At block 308, control circuit 206 identifies the Vpace delivered at block 322 directly following a sensed atrial event that is identified as an early atrial event at block 702. The Vpace following the early atrial event is identified as the ventricular event ending a ventricular rate interval used to update the actual ventricular rate interval at block 308. When the rate smoothing interval is set at block 310, following the ventricular pacing pulse delivered directly after the early atrial event, the rate smoothing interval may be set by adding the extended rate smoothing increment (block 704) to the updated actual ventricular rate interval (block 308). To illustrate, if the rate smoothing interval is normally set at block 310 to be 100 ms longer than the updated actual ventricular rate interval, the extended rate smoothing increment may be 150 ms or 200 ms. In some examples, the extended rate smoothing increment is twice the normal increment added to the actual ventricular rate interval to set the rate smoothing interval.

When the sensed A4 event is not identified as an early event ("no" branch of block 702), control circuit 206 may return directly to block 308, without triggering the use of an extended rate smoothing increment at block 704. As such, control circuit 206 may add one rate smoothing increment to the actual ventricular rate interval to set the rate smoothing pacing interval after atrial events that are not identified as being early atrial events and add another, longer rate smoothing increment to the actual ventricular rate interval when the atrial event is identified as being an early event, possibly a PAC or an oversensed A3 signal.

In other examples, the extended rate smoothing increment may be determined based on the prematurity of the early atrial event. For example, if the Vp-Vp interval including the early atrial event is X ms shorter than the most recently updated actual ventricular rate interval, X ms may be added to the rate smoothing interval. In some examples, the extended rate smoothing interval following an early atrial event is determined as the updated actual ventricular rate interval plus a fixed rate smoothing increment plus an extended rate smoothing increment determined based on the prematurity of the early atrial event.

Figure 10:
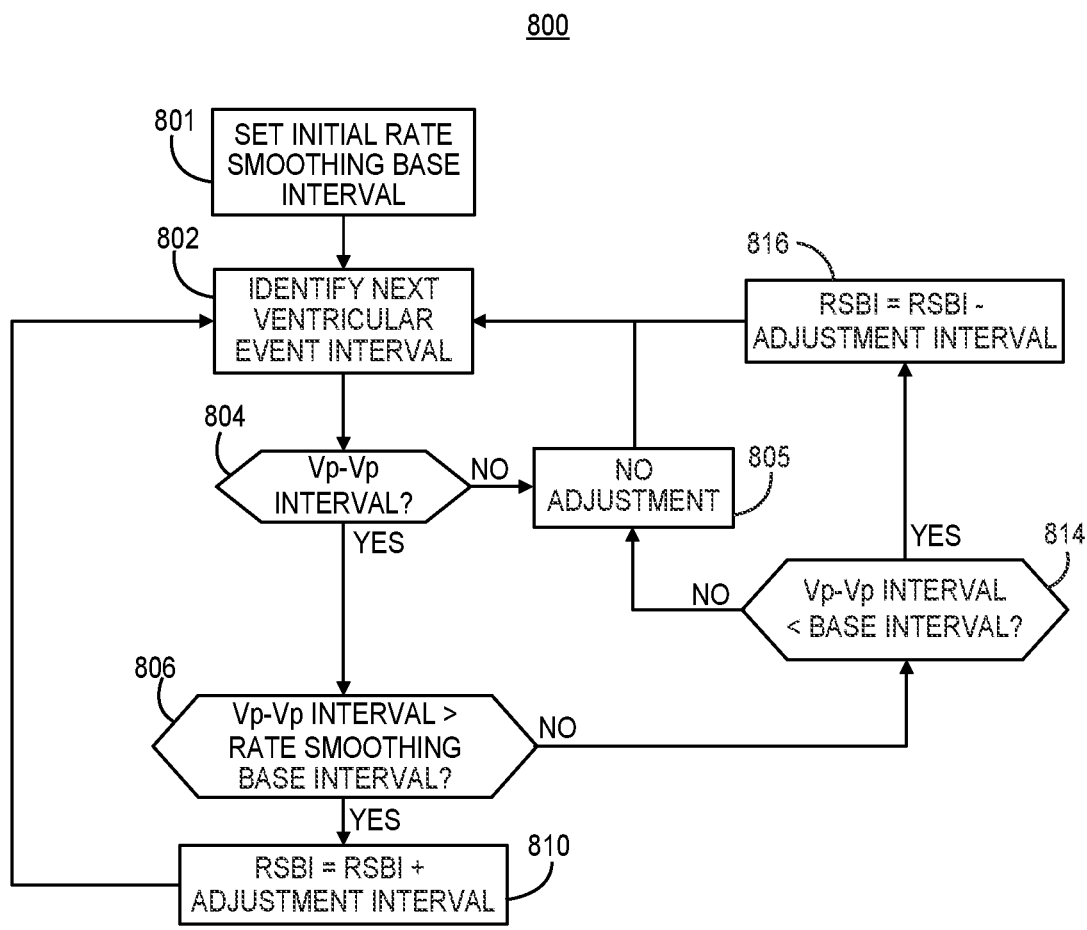
FIG. 10 is a flow chart of a method that may be performed by pacemaker 14 for updating the rate smoothing interval according to some examples.

FIG. 10 is a flow chart 800 of a method that may be performed by pacemaker 14 for updating a rate smoothing base interval based on the actual ventricular rate interval, e.g., after each Vp-Vp interval. The method of FIG. 10 may be performed at block 310 of FIGS. 6 and 9 for setting the rate smoothing interval. In examples described above, the rate smoothing interval may be set by adding a predetermined increment (which may be extended in response to an early atrial sensed event) to an actual ventricular pacing rate interval determined from a predetermined number of ventricular event intervals. In the example of FIG. 10, a rate smoothing base interval is determined based on the actual ventricular rate interval, and the rate smoothing interval is set by adding an increment to the rate smoothing base interval at block 310 of FIGS. 6 and 9. The rate smoothing base interval may be determined using a single, most recent Vp-Vp interval. The rate smoothing base interval is adjusted after each Vp-Vp interval, based on a comparison between the rate smoothing base interval and the Vp-Vp interval, to track the actual Vp-Vp intervals.

At block 802, control circuit 206 may set the rate smoothing base interval to an initial value. In some examples, the rate smoothing base interval is initially set according to the programmed lower rate interval, e.g., to the lower rate interval less the rate smoothing increment. Without actual pacing rate history, e.g., at the time of initial implant, an actual ventricular pacing rate is not available for basing the rate smoothing interval on. As such, the rate smoothing base interval may be initialized according to the programmed lower rate interval (LRI) at block 801. Referring to FIG. 9, prior to a first ventricular paced interval, an actual ventricular rate interval based only on Vp-Vp intervals cannot be updated at block 308. Control circuit 206 may start the rate smoothing interval set initially to the LRI in response to a Vpace (block 304). From that point on, the rate smoothing interval set at block 310 may be adjusted based on an actual ventricular rate interval that is updated at block 308 in response to a Vp-Vp interval.

At block 802 of FIG. 10, a ventricular event interval is identified. When the ventricular event interval includes a sensed intrinsic R-wave, resulting in an Rsense-Rsense interval, Rsense-Vp interval or a Vp-Rsense interval, a Vp-Vp interval is not identified at block 804. No adjustment to the rate smoothing base interval is performed at block 805. The rate smoothing interval may stay the same, i.e., equal to a previously set rate smoothing interval and is not started in response to a sensed intrinsic R-wave. However, when two consecutive ventricular pacing pulses occur, i.e., when a Vp-Vp interval occurs, as determined at block 804, control circuit 206 determines the actual Vp-Vp interval as the actual ventricular rate interval and compares it to the current value of the rate smoothing base interval at block 806. The rate smoothing base interval is the rate smoothing interval less the rate smoothing increment, (e.g., less 100 ms or other rate smoothing increment being used to set the rate smoothing interval). Initially, the rate smoothing base interval may be set to the lower rate interval less the rate smoothing increment. Based on the comparison at block 806, control circuit 206 updates the rate smoothing base interval to track the actual Vp-Vp interval so that the rate smoothing interval tracks the actual ventricular pacing rate during atrial synchronized ventricular pacing.

The Vp-Vp interval identified at block 804 may end with a ventricular pacing pulse that is delivered at the current rate smoothing interval (no A4 event sensed) or at an AV interval following a sensed A4 event. When an A4 event is sensed, the Vp-Vp interval identified at block 804 may be equal to, greater than or less than the rate smoothing base interval depending on the timing of the sensed A4 event following the leading Vpace and the duration of the AV interval. The control circuit 206 may start the AV interval in response to the sensed A4 event and inhibit the ventricular pacing pulse scheduled at the expiration of the rate smoothing interval. In this way, the ventricular pacing pulse is delivered synchronized to the sensed A4 event, which may be earlier, at or later than the rate smoothing base interval.

If the actual Vp-Vp interval identified at block 804 is greater than the current rate smoothing base interval ("yes" branch of block 806), the A4 event may be sensed relatively late (e.g., a slowing atrial rate) and/or the AV interval may be relatively long resulting in a Vpace that ends the Vp-Vp interval that is longer than the rate smoothing base interval. When the Vp-Vp interval is greater than the rate smoothing base interval, the rate smoothing base interval is updated at block 810 to be the current rate smoothing base interval plus an adjustment interval, e.g., plus 7.8 ms, to account for a possible slowing of the atrial rate. This rate smoothing base interval is used to set the rate smoothing interval started at block 310 of FIG. 9, from the ending Vpace of the Vp-Vp interval. The rate smoothing interval is set equal to the base interval plus the rate smoothing increment, e.g., plus 100 to 200 ms. Even when the ventricular pacing pulse scheduled at the rate smoothing interval is withheld, due to a sensed A4 event starting an AV interval, the rate smoothing base interval is updated and used in setting the next rate smoothing interval according to a comparison between the actual Vp-Vp interval and the current rate smoothing base interval.

When an A4 event is not sensed, the Vp-Vp interval may be equal to the rate smoothing interval, in which case the actual Vp-Vp interval identified at block 804 is greater than the rate smoothing base interval by the rate smoothing increment ("yes" branch of block 806). The rate smoothing base interval is increased by an adjustment interval, e.g., 7.8 ms or more, to effectively increase the rate smoothing interval and promote A4 event sensing on the next ventricular cycle. The rate smoothing base interval may be increased up to, but not greater than, the lower rate interval less the rate smoothing increment, in which case the rate smoothing interval is set to the lower rate interval. In other examples, the rate smoothing base interval may be increased up to the lower rate interval, however, the rate smoothing interval is limited to a maximum interval of the lower rate interval and not set using an increment that would cause the rate smoothing interval to exceed the lower rate interval.

When the Vp-Vp interval is not greater than the rate smoothing base interval ("no" branch of block 806), the Vp-Vp interval may include a sensed A4 event and the actual Vp-Vp interval may be shorter than or equal to the rate smoothing base interval. When the Vp-Vp interval is equal to the rate smoothing base interval at block 814 ("no" branch), no adjustment to the rate smoothing base interval is made at block 805. The rate smoothing interval remains unchanged. When the Vp-Vp interval is less than the rate smoothing base interval ("yes" branch of block 814), control circuit 206 updates the rate smoothing base interval at block 816 by decreasing the current rate smoothing base interval by the adjustment interval, e.g., the current base interval minus 7.8 ms or more. In this case, the sensed A4 event triggers the Vpace at an interval shorter than the rate smoothing base interval, which may indicate an increasing atrial rate. The rate smoothing base interval is updated to a shortened interval and is used for setting the next rate smoothing interval at block 310 of FIGS. 6 and 9 to avoid sudden changes in ventricular rate while still promoting A4 event sensing.

In this way, the rate smoothing interval is updated based on an actual ventricular pacing rate (each Vp-Vp interval) and started upon delivery of each Vpace. The actual ventricular pacing rate may be determined as one Vp-Vp interval that is used to update the rate smoothing base interval each pacing cycle. By tracking the actual ventricular pacing rate through adjustments to the rate smoothing base interval, the rate smoothing interval may be increased beat-by-beat (excluding beats including a sensed intrinsic R-wave) until the LRI is reached as long as the actual Vp-Vp interval is increasing. The rate smoothing interval may be decreased beat-by-beat as long as the actual Vp-Vp interval is less than the rate smoothing interval, corresponding to an increasing atrial rate. When the current ventricular cycle is not a Vp-Vp interval, e.g., either or both of the leading and ending ventricular events are sensed R-waves, control circuit 206 may return to block 802 without adjusting the rate smoothing base interval. The rate smoothing base interval may not be adjusted based on intervals that include a sensed R-wave or when the actual Vp-Vp interval equals the rate smoothing base interval (e.g., within a predetermined range of the rate smoothing base interval). In these two cases, the rate smoothing base interval, and a subsequent rate smoothing interval set in response to a delivered Vpace, may be held at their current values.

Figure 11:
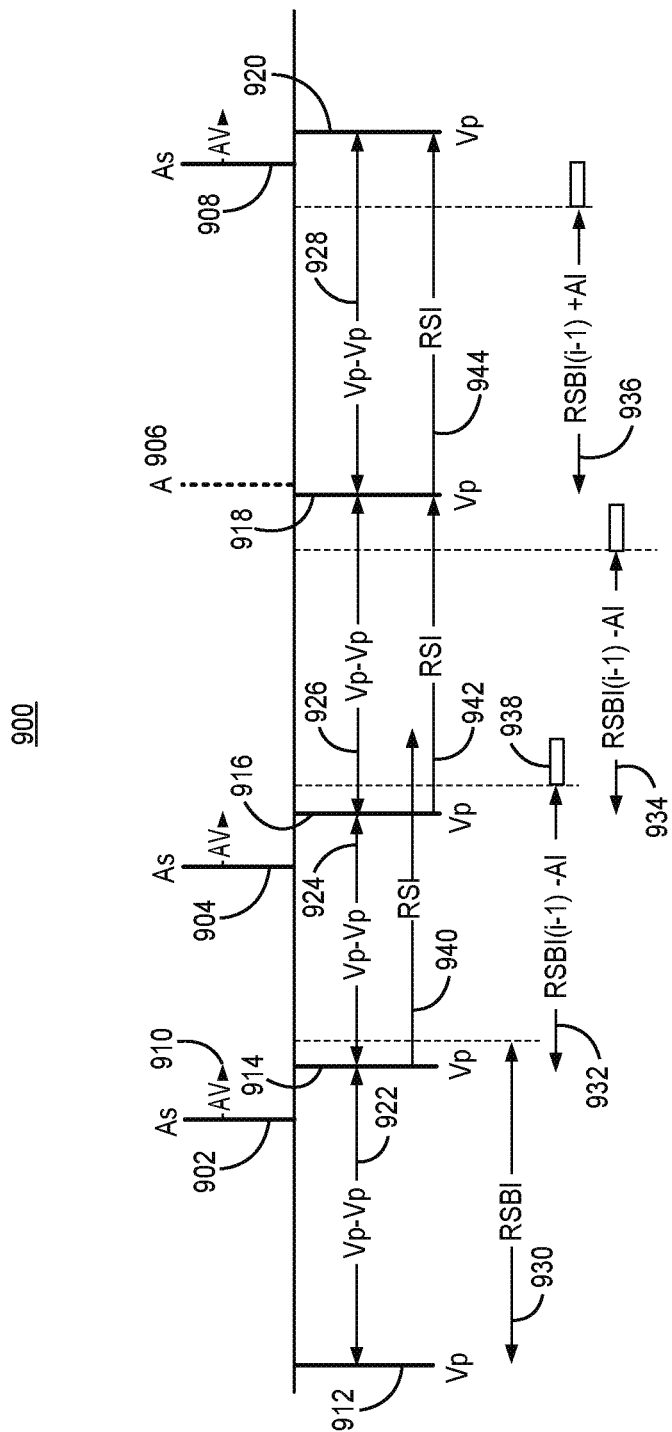
FIG. 11 is a timing diagram depicting sensed atrial systolic events, ventricular pacing pulses, and corresponding pacing control time intervals for providing pacing rate smoothing during atrial synchronized ventricular pacing according to one example.

FIG. 11 is a timing diagram 900 depicting sensed atrial systolic events, ventricular pacing pulses, and corresponding pacing control time intervals for providing pacing rate smoothing during atrial synchronized ventricular pacing according to one example. Control circuit 206 starts an AV interval 910 in response to each sensed atrial systolic event 902, 904 and 908, which may be A4 events sensed from the motion signal. A first Vp-Vp interval 922 is defined by leading Vpace 912 and ending Vpace 914, which is delivered at AV interval 910 following the sensed A4 event 902. Vp-Vp interval 922 is determined as an actual ventricular rate interval. A first rate smoothing base interval (RSBI) 930 is compared to the actual Vp-Vp interval 922. Since the RSBI 930 is greater than the Vp-Vp interval 922, the next RSBI 932 is decreased by subtracting the adjustment interval (AI) from the first RSBI 930, e.g., RSBI=RSBI(i−1)−7.8 ms in one example.

This new RSBI 932 is used to set the rate smoothing interval (RSI) 940 equal to the adjusted RSBI 932 plus the rate smoothing increment 938. Since another A4 event 904 is sensed before the RSI 940 expires, the next Vpace 916 is delivered at the AV interval 910 following the sensed A4 event 904. The resulting actual Vp-Vp interval 924 is compared to the current RSBI 932. Since the current RSBI 932 is greater than the actual Vp-Vp interval 924, the next RSBI 934 is also decreased by subtracting the adjustment interval. The next RSI 942 is set to the adjusted RSBI 934 plus the rate smoothing increment 938.

In this example, a decrease in the atrial rate on the next beat results in the next A4 event 906 to occur later than the expiration of the RSI 942 and go unsensed by control circuit 206. A Vpace 918 is delivered upon expiration the RSI 942. The resulting actual Vp-Vp 926 is longer than the current RSBI 934 (by the rate smoothing increment 938). As such, the next RSBI 936 is increased by adding the adjustment interval. The next RSI 944 is set to the increased RSBI 936 plus the rate smoothing increment 938. This increased RSI 944 allows the next A4 event 908 to be sensed before expiration of the RSI 944 so that the final Vpace 920 shown in FIG. 11 is delivered synchronized to the sensed A4 event 908 at the AV interval 910.

As shown in FIG. 11, the RSBI tracks the actual ventricular rate interval, determined as a single Vp-Vp interval in this example, and the RSI is set as the RSBI plus the rate smoothing increment. The RSBI may be increased or decreased depending on the actual Vp-Vp interval so that the RSI also tracks the actual ventricular pacing rate during A4 event sensing but, being set by a rate smoothing increment longer than the RSBI, the RSI promotes sensing of the A4 events when sensing of the A4 event(s) is temporarily lost due to a change in atrial rate. It is recognized that in other examples, the current RSBI may be compared to an actual ventricular rate interval that is determined from more than one Vp-Vp interval. For example, the current RSBI may be compared to a median or mean value or two or more most recent Vp-Vp intervals.

The adjustment interval used to adjust the RSBI based on the comparison to the actual ventricular rate interval may be programmable and may range from 5 ms to 20 ms as examples. The adjustment interval may be fixed (until reprogrammed by a user) or may be automatically adjusted in some examples. For instance, after a threshold number of consecutive increases in the RSBI due to pacing at the RSI, the AI may be increased to provide a larger step increase in the RSI to promote restoration of A4 sensing. After a threshold number of consecutive decreases in the RSBI due to shortening Vp-Vp intervals that include A4 sensed events, the AI may be increased so that the RSBI is shortened at a faster rate when the atrial rate is increasing relatively quickly. In other examples, the adjustment interval used to decrease the RSBI and the adjustment interval used to increase the RSBI may be set to different intervals and/or one may be variable with the other fixed. For example, the adjustment interval used to increase the RSBI may be adjustable to allow a faster increase in the RSI when A4 sensing is lost but the adjustment interval used to decrease the RSBI may remain fixed to avoid rapid shortening of the RSI that may preclude A4 event sensing during a varying atrial rate.

Additionally or alternatively, the rate smoothing increment 938 may be a fixed, user-programmable or automatically adjusted interval. As described above, the rate smoothing increment 938 may be extended, e.g., doubled, when the sensed A4 event is determined to occur early after a ventricular pacing pulse. In other examples, the rate smoothing increment 938 may be automatically increased or decreased after a threshold number of ventricular pacing pulses delivered at the RSI to promote a more rapid adjustment of the Vp-Vp interval in the absence of sensed A4 events and thereby promote earlier recovery of the A4 event sensing.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
   a memory configured to store a base interval, an adjustment interval and a rate smoothing increment;
   a sensor configured to produce a sensor signal;
   a pulse generator configured to generate ventricular pacing pulses; and
   a control circuit coupled to the sensor and the pulse generator and configured to:
   detect atrial events from the sensor;
   control the pulse generator to deliver ventricular pacing pulses synchronized to the atrial events detected from the sensor signal;
   determine actual Vp-Vp intervals where each actual Vp-Vp interval extends between two consecutively delivered ventricular pacing pulses;
   adjust the base interval stored in the memory by, based on the actual Vp-Vp intervals, adding or subtracting the adjustment interval to or from the base interval;
   determine a rate smoothing interval as the adjusted base interval plus the rate smoothing increment; and
   start the rate smoothing interval to schedule a next ventricular pacing pulse in response to the pulse generator delivering a ventricular pacing pulse.

2. The medical device of claim 1 wherein the control circuit is further configured to adjust the base interval by the adjustment interval wherein the adjustment interval is less than the rate smoothing increment.

3. The medical device of claim 2 wherein the control circuit is further configured to adjust the base interval by the adjustment interval by:
comparing an actual Vp-Vp interval of the determined actual Vp-Vp intervals to a current value of the base interval; and
a) increasing the base interval by adding the adjustment interval when the actual Vp-Vp interval is greater than the current value of the base interval; or
b) decreasing the base interval by subtracting the adjustment interval when the actual Vp-Vp interval is less than the current value of the base interval.

4. The medical device of claim 3 wherein the control circuit is further configured to adjust the base interval in response to each actual Vp-Vp interval of the determined Vp-Vp intervals that is not equal to a current value of the base interval.

5. The medical device of claim 1 wherein the control circuit is further configured to:
determine that the rate smoothing interval expires without detecting an atrial event from the sensor signal;
control the pulse generator to deliver the next ventricular pacing pulse in response to the rate smoothing interval being expired; and
adjust the base interval again by increasing the adjusted base interval by the adjustment interval in response to the rate smoothing interval being expired without detecting the atrial event from the sensor signal.

6. The medical device of claim 1 wherein the control circuit is further configured to adjust the base interval up to a maximum value equal to a programmed lower rate interval less the rate smoothing increment.

7. The medical device of claim 1 further comprising a sensing circuit configured to sense ventricular event signals attendant intrinsic ventricular depolarizations;
wherein the control circuit is further configured to start a programmed pacing lower rate interval in response to the sensing circuit sensing a ventricular event signal.

8. The medical device of claim 1 wherein:
the memory is further configured to store a programmed lower pacing rate interval; and
the control circuit is further configured to set a starting value of the base interval to the programmed lower pacing rate interval.

9. The medical device of claim 1 wherein the sensor comprises an accelerometer configured to produce the sensor signal as an acceleration signal.

10. The medical device of claim 1 further comprising:
a housing enclosing the sensor, the pulse generator and the control circuit; and
a pair of pacing electrodes spaced apart along the housing and coupled to the pulse generator for delivering the ventricular pacing pulses.

11. A method comprising:
storing in a memory of a medical device a base interval, an adjustment interval, and a rate smoothing increment;
detecting atrial events from a sensor signal;
delivering ventricular pacing pulses by a pulse generator, the ventricular pacing pulses comprising ventricular pacing pulses that are synchronized to the atrial events detected from the sensor signal;
determining actual Vp-Vp intervals where each actual Vp-Vp interval extends between two consecutively delivered ventricular pacing pulses;
adjusting the base interval by, based on the actual Vp-Vp intervals, adding or subtracting the adjustment interval to or from the base interval;
determining a rate smoothing interval as the adjusted base interval plus the rate smoothing increment; and
in response to a delivered ventricular pacing pulse, starting the rate smoothing interval to schedule a next ventricular pacing pulse.

12. The method of claim 11 further comprising adjusting the base interval by the adjustment interval wherein the adjustment interval is less than the rate smoothing increment.

13. The method of claim 12 further comprising adjusting the base interval by the adjustment interval by:
comparing an actual Vp-Vp interval of the determined actual Vp-Vp intervals to a current value of the base interval stored in the memory; and
c) increasing the base interval by adding the adjustment interval when the actual Vp-Vp interval is greater than the current value of the base interval; or
d) decreasing the base interval by subtracting the adjustment interval when the actual Vp-Vp interval is less than the current value of the base interval.

14. The method of claim 13 further comprising adjusting the base interval in response to each actual Vp-Vp interval of the determined Vp-Vp intervals that is not equal to a current value of the base interval.

15. The method of claim 11 further comprising:
determining that the rate smoothing interval expires without detecting an atrial event from the sensor signal;
delivering the next ventricular pacing pulse in response to the rate smoothing interval being expired; and
adjusting the base interval again by increasing the adjusted base interval by the adjustment interval in response to the rate smoothing interval being expired without detecting the atrial event from the sensor signal.

16. The method of claim 11 further comprising adjusting the base interval up to a maximum value equal to a programmed lower rate interval less the rate smoothing increment.

17. The method of claim 11 further comprising:
sensing ventricular event signals attendant intrinsic ventricular depolarizations; and
starting a programmed pacing lower rate interval in response to sensing a ventricular event signal.

18. The method of claim 11 further comprising setting the base interval to a starting value equal to a programmed lower pacing rate interval.

19. The method of claim 11 further comprising sensing an acceleration signal by an accelerometer,
wherein detecting the atrial events from the sensor signal comprises detecting the atrial events from the acceleration signal.

20. The method of claim 11 wherein delivering the ventricular pacing pulses comprises delivering the ventricular pacing pulses via a pair of pacing electrodes spaced apart along a housing of a medical device that encloses the pulse generator.

* * * * *